United States Patent [19]

Ransberger et al.

[11] Patent Number: 5,002,766

[45] Date of Patent: Mar. 26, 1991

[54] USE OF CATABOLIC ENZYMES FOR CONTROLLING THE ACQUIRED IMMUNE DEFICIENCY SYNDROME (AIDS) AND ITS PRECURSORS (LAS, ARC)

[75] Inventors: Karl Ransberger, Grünwald; Gerhard Stauder, Wolfratshausen, both of Fed. Rep. of Germany

[73] Assignee: Mucos Pharma GmbH & Co., Geretsried, Fed. Rep. of Germany

[21] Appl. No.: 248,427

[22] Filed: Sep. 23, 1988

[30] Foreign Application Priority Data

Sep. 30, 1987 [EP] European Pat. Off. ............ 87114289

[51] Int. Cl.$^5$ ...................... A61K 37/62; A61K 37/54; A61K 35/78; A61K 35/55
[52] U.S. Cl. .................. 424/94.2; 424/94.21; 424/94.6; 424/94.65; 424/580; 424/195.1
[58] Field of Search ................ 424/94.2, 94.21, 94.6, 424/195.1, 94.65, 95, 110; 435/226

[56] References Cited

U.S. PATENT DOCUMENTS 4,571,336  2/1986  Houck et al. ......................... 424/95
4,591,504  5/1986  Ohnishi et al. ...................... 435/226
4,826,680  5/1989  Jaeger ................................. 424/95

FOREIGN PATENT DOCUMENTS 72947  2/1983  European Pat. Off. ........... 424/94.2

*Primary Examiner*—Jacqueline Stone
*Attorney, Agent, or Firm*—Reed Smith Shaw & McClay

[57] ABSTRACT

The therapy approaches known so far for the treatment of the acquired immune deficiency syndrome (AIDS) and its precursors (LAS and ARC) and the secondary diseases related thereto such as opportunistic infections and malignant tumours are either directed against the proliferation of the virus in the body or against the pathogenic organisms of the opportunistic infections or they are selected from the known agents against malignant tumours. So far all therapies did not have any significant success.

The new use of catabolic enzymes for the therapy of AIDS and its precursors (LAS and ARC) is made available, with which completely unexpected successes can be achieved in the improvement of the condition of the patient.

13 Claims, No Drawings

USE OF CATABOLIC ENZYMES FOR CONTROLLING THE ACQUIRED IMMUNE DEFICIENCY SYNDROME (AIDS) AND ITS PRECURSORS (LAS, ARC)

The invention relates to the use of catabolic enzymes for controlling the acquired immune deficiency syndrome (AIDS) and its precursors (LAS, ARC).

The said phases of the disease comprise the phases WR1 to WR6 according to the Water Reed classification. The abbreviations LAS and ARC stand for "AIDS-related complex" or "lymphadenopathy syndrome".

The aquired immune deficiency syndrome AIDS and its precursors (LAS, ARC) are a virus disease. It is attributable to a virus which belongs to the group of the retroviruses very prevalent in the animal kingdom and is called human immunodeficiency virus (HIV). Disturbances of the entire immunodefense mechanisms result from the HIV infection, because above all the helper cells of the T system of the specific immunodefense and thus the key positions of immunodefense are affected. The T4 or helper cells affected by the HIV infection are prevented from carrying out their central role in the regulation of the immunoresponse. The disturbing effect caused by the HIV virus infection can obviously consist in a direct or indirect reduction of said cells.

After HIV infections, disturbances of the balance between the different T cell populations are observed, the balance between the T4 and T8, between helper and suppressor cells, seems to be in particular disturbed. The T4/T8 ratio, which is normally 1.4 to 2.0 is shifted in favour of the T8 cells. It is reversed so that a T4/T8 ratio of 1:2 or of still lower values occurs. The HIV-induced, persistent T4 cell reduction entails that pathogenic organisms which are harmless if there is a normal balance between the different T cell populations meet with favourable milieu conditions in patients in which there is the described disproportion between T4 and T8 cells. The pathogenic organisms may be viruses, bacteria, protozoans or fungi. These so-called opportunistic infections cause very different clinical pictures in HIV patients. The complete picture of AIDS includes besides the HIV infection opportunistic persistent or recurring diseases which point to defects of the T immune system. Different inflammatory diseases triggered by different pathogenic organisms are frequently found in persons suffering from AIDS.

Carcinomatous degenerations of tissue are furthermore observed, which otherwise occur very rarely such as the so called Kaposi's sarcoma and other malignant diseases such as lymphomas of the brain, non-Hodgkin's and Burkitt lymphomas.

The lymphopenia ($<1000/mm^3$), T helper cell disintegration ($<400/mm^3$), anaemia, leucopenia and thrombocytopenia, missing in vitro stimulatability of the lymphocytes and the missing reactivity to "recall" antigens which are detectable in patients with a complete AIDS picture are objective criteria for the disturbance of the reticuloendothelial system (RES).

Increased immunoglobulin titres of IgA, IgG and IgM are moreover found in patients with a complete AIDS picture.

There are furthermore clues as to that the immunity complex (IC) levels may be increased in persons suffering from AIDS. According to Lightfoote et al. (1985) special IgA containing antigen-antibody complexes are characteristic of persons suffering from AIDS.

The pathogenicity of the immunity complexes are based on their interaction with different components of the specific and unspecific immunodefense. Besides the inhibition of the macrophages, the stimulation of T suppressor cells, the thrombogenic and erythrocyte-aggregating and in particular the complement-activating properties form part of them, due to which inflammatory diseases and tissue lesions occur.

At present it has not been decided whether AIDS and its precursors (LAS, ARC) are autoaggression or immunity complex diseases on the basis of a cytotoxic reaction, namely an allergic reaction of the type II.

The numerous publications on the aetiological mechanisms in AIDS and its precursors (LAS, ARC) are not without contradictions. As is revealed by the representation of Rieber (1986) the AIDS virus has several possibilities of interfering with central functions of the immunity system.

The therapeutic efforts in the treatment of the primary disease, the T4 cell disintegration, have so far been unsuccessful. A causal treatment of the HIV infection and the immunodeficiency derived from it is clinically not possible at present. The treatments carried out at present focus on the one hand on the inhibition of virus proliferation and on the other hand on the secondary diseases found in AIDS and its precursors (LAS, ARC), namely the opportunistic infections and the malignant processes (Goebel et al., 1985).

Although more than 100 substances (Koch, 1987) for controlling the initial virus infection and the secondary diseases connected therewith have been used and tested all over the world almost hectically, the success achieved so far is discouraging.

The invention was based on the object to make an effective control of the acquired immune deficiency syndrome (AIDS) and its precursors (LAS, ARC) and the secondary diseases connected with it available.

The object is solved by using catabolic enzymes for controlling the acquired immune deficiency syndrome (AIDS) and its precursors (LAS, ARC) and the secondary diseases connected with it.

Immunity complexes become pathogenic if they are bonded to cells. The immunodeficiency is synergistically intensified if the activity of macropahages and natural killer cells (NK) is reduced thereby. Due to the thus increasing concentration of immunity complexes the activity of macrophages is further blocked.

The use of catabolic enzymes, in particular of hydrolytic or proteolytic enzymes, for the therapy of different diseases has been known since the fifties, the use of the enzymes having been described in the treatment of acute and chronic inflammations, in the case of circulatory disturbances and in tumour treatment.

Although the in vitro disintegration of soluble immunity complexes by hydrolytic or proteolytic enzymes had been known, it was nevertheless surprising that the actually observed, significant improvement of the condition occurred with AIDS patients by the use of the known catabolic enzymes according to the invention.

Due to the catabolic enzymes used according to the invention, immunity complexes are digested by cleaving the Fc arm of the antibodies. In the still unclarified aetiology of the immunodeficiency disease the resultant improvement of the entire immunity system of the patient was nevertheless not to be expected. An explanation of the observed positive effect may reside in that due to the elimination of the immunity complexes by the enzymes used according to the invention an improvement of the T4/T8 ratio is achieved, whereby the endogenic defence can control the pathogenic antigens (the HIV virus or its components) more effectively. The cells containing viruses can then be better eliminated by the natural killer cells.

Due to the used hydrolytic or proteolytic enzymes macrophages and natural killer cells are directly activated, whereby the immunodefense is still increased additionally.

A further known principle of action of the used enzymes is based on the splitting of macromolecular catabolites and necrotically formed cell detritus.

The surprisingly positive effect of the use of the enzymes used according to the invention may be based on the fact that the blockage of the immunoregulatory mechanisms caused by the immunity complexes and the disturbed phagocytosis of the cells of the reticuloendothelial system (RES cells) is cancelled. Thus the enzyme therapy entails the modulation and stimulation of the specific and unspecific immunodefense.

The used enzymes have, moreover, fibrinolytic properties due to which the destruction of the fibrin envelope occurs, by means of which circulating immunity complexes may be caused to sediment and thus can adhere better as secondarily tissue-fixed immunity complexes. The actual pathogenicity of the immunity complexes resides in this process, because the adhered, tissue-fixed immunity complexes may activate the complement cascade up to the end phase, the cytolytic complex.

Due to these hydrolytic remobilization phenomena by means of which also immunity complexes situated primarily in the tissue may be disintegrated, a decrease of the inflammatory process occurs. There is a highly complex inflammatory process present in the immune deficiency syndrome AIDS due to the most different antigen-antibody complexes. As was shown by Jäger et al. 1987 with Water Reed (WR) classified HIV-positive patients, the mean immunity complex titre increases significantly in different WR phases. A maximum of immunity complex titres is reached. The humoral immunity system is also weakened in terminal AIDS patients, due to which the immunity complex titres are again decreased.

However, the described observations cannot be clearly interpreted and show a very complex interaction of antigen-antibody complexes of different origin. The immunity complexes contain partly HIV or components of HIV which originate from the HIV infection. The immunity complexes may brought about by the opportunistic infections and malignant growth processes.

Besides the remarkable therapeutical and unexpected effect of the use of the enzymes according to the invention, this use has furthermore the advantage that also in the case of a long-term use no detrimental side effects occur as is known from the use of said enzymes in the fields already tried out.

The enzymes used according to the invention may preferably be papain, pancreatin, bromelin, lipase, amylase, tripysin, α-chymotrypsin or Serratia peptidase.

Papain is a proteolytic enzyme disintegrating up to the amino acids which is obtained from the milky exudate of the unripe, pulpy fruits of the melon tree Carica papaya.

Pancreatin is obtained from pig or bovine pancreas.

Bromelin is a proteolytically active enzyme from the squeezed juice of pineapple.

Lipases belong to the sub-group of the esterases and are obtained from pancreas or the fungus Rhizopus arrhizus.

Amylases are glycoside splitting enzymes which are e.g. isolated from pancreas or special microorganisms.

Trypsin and α-chymotrypsin are proteolytic enzymes which are also formed in the pancreas and have already been used therapeutically in connection with other enzymes.

*Serratia peptidase* can be obtained from a microorganism of the species Serratia.

Rutin which may furthermore be added to the enzyme mixture belongs to the flavonoid glycosides.

Calf thymus factors which may also be possibly added to the used enzyme mixtures are isolated from thymus glands.

The special effectiveness of the described substances becomes apparent if two or more of said enzymes are used in combination.

Adjuvants as they are customarily used, preferably mannitol, may be added to the formulation finally used.

A mixture showed special effectiveness, which was obtained from fractionated hydrolysates of bovine pancreas, calf thymus, Pisum sativum and Lens esculenta and papain and mannitol, namely in the respective amounts of 1 to 10, preferably 8 mg, 1 to 10, preferably 4 mg, 1 to 10, preferably 4 mg, 1 to 10, preferably 4 mg, 1 to 10, preferably 2 mg and 10 to 100, preferably 78 mg.

A further embodiment of the enzyme mixture according to the invention contains a mixture of 10 to 30, preferably 24 mg, trypsin, 1 to 10, preferably 1 mg, α-chymotrypsin, 40 to 100, preferably 60 mg, papain, 50 to 200, preferably 100 mg, pancreatin, 20 to 100, preferably 45 mg, bromelin, 5 to 50, preferably 10 mg, lipase, 5 to 50, preferably 10 mg amlyase and 10 to 100, preferably 50 mg rutin.

A further embodiment consists of a mixture of trypsin, α-chymotrypsin, papain and calf thymus in the respective amounts of 1 to 10, preferably 4 mg, 1 to 10, preferably 4 mg, 5 to 50, preferably 10 mg and 1 to 10, preferably 3 mg in ampoules or respectively 10 to 100, preferably 40 mg, 10 to 100, preferably 40 mg, 50 to 500, preferably 100 mg and 10 to 100, preferably 40 mg in enema tablets or tablets to be taken orally.

A therapy method for the treatment of the immune deficiency syndrome AIDS and its precursors (LAS, ARC) is shown with the described enzyme mixtures, which is completely novel and has shown unexpectedly positive results.

This is explained in the following in detail by means of clinical tests.

CARRYING OUT OF CLINICAL TESTS

| WOBE-MUGOS ® Enzyme mixture I | Ampoules | Anema tablets | Oral tablets | WOBENZYM ® Enzyme mixture II |
|---|---|---|---|---|
| Enzymes contained | 1 ampoule | 1 tablet | 1 tablet | 1 coated tablet |
| Trypsin | 4 mg | 40 mg | 40 mg | 24 mg |
| α-chymotrypsin | 4 mg | 40 mg | 40 mg | 1 mg |
| Papain | 10 mg | 100 mg | 100 mg | 60 mg |
| Calf thymus | 3 mg | 40 mg | 40 mg | — |
| Pancreatin | — | — | — | 100 mg |
| Bromelin | — | — | — | 45 mg |

| WOBE-MUGOS® Enzyme mixture I | Ampoules | Anema tablets | Oral tablets | WOBENZYM® Enzyme mixture II |
|---|---|---|---|---|
| Lipase | — | — | — | 10 mg |
| Amylase | — | — | — | 10 mg |
| Rutin | — | — | — | 50 mg |

Patients were treated which showed a positive test for HIV and clinical symptoms and/or signs of AIDS, ARC (AIDS-related complex) or LAS (lymphadenopathy syndrome).

The tests for HIV were carried out in accordance with the international standards and the patients were selected if at least two different test showed a positive proof of the HIV infection.

DOSAGE AND APPLICATION

1st to 4th week up to 3× weekly 1 ampoule WOBE-MUGOS® per injection on days without injection up to 15 tablets WOBE-MUGOS® per day alternatively up to 15 WOBE-MUGOS® anema tablets per rectum accompanied by up to 30 coated tablets WOBENZYM® per day (i.e. up to 10 coated tablets 3× daily or 6 coated tablets 5× daily, etc).

as of the 5th week daily up to 15 tablets WOBE-MUGOS® per day;

alternatively up to 5 WOBE-MUGOS® enema tablets per rectum accompanied by up to 30 coated tablets WOBENZYM® per day (e.g. up to 10 coated tablets 3× daily or 6 coated tablets 5 times daily, etc.).

The therapy is carried out for at least 3 months; after this period of time an individual decision is made on the continuation of the therapy depending upon success and tolerance.

The T4/T8 ratio was clearly improved with at least 18 patients treated according to this record. At the same time it was possible to improve the clinical symptoms lastingly over a period of time of at least 6 months.

The course of the disease and the therapy of the Patient R is indicated as a drastic example of the amazing effect of a treatment with the enzyme mixtures according to the invention as it was described above. The patient R. had a T4/T8 ratio of <0.06 and was also considered as a hopeless case and was connected to continuous infusion. After the aforementioned therapy (therapy duration: beginning of July 1987 to mid-September 1987) the T4/T8 ratio was improved to >1. Since the end of August the patient has been pursuing his normal work and is again fully active sexually.

List of Publications

1. Goebel F.D., et al., Zur Pathophysiologie und Klinik des erworbenen Immundefektsyndroms AIDS), Tempo Medical, special issue Neueinführungen, December 1985 (1985), 8 to 13

2. Jäger H., et al. Circulating Immune Complexes in HIV Infection, 2nd International Symposium on Immunobiology in Clinical Oncology and Immune Dysfunctions, Nice, April 4 to 7, 1987

3. Koch M., AIDS—vom Molekül zur Pandemie, Spektrum der Wissenschaft, Heidelberg, (1987)

4. Rieber E.P., Störungen der Immunantwort bei LAS und AIDS, Münch. Med. Wschr. 128 (1986) 463 to 466

What is claimed is:

1. A method of treating a patient having acquired immune deficiency syndrome, AIDS, or its precursors, lymphadenopathy syndrome, LAS, or AIDS-related complex, ARC, comprising administering a composition comprising trypsin, α-chymotrypsin, papain, pancreatin, bromelin, lipase, amylase, and rutin to the patient.

2. The method of claim 1, wherein said composition comprises a mixture of about 10 to 30 mg trypsin, about 1 to 10 mg α-chymotrypsin, about 40 to 100 mg papain, about 50 to 200 mg pancreatin, about 20 to 100 mg bromelin, about 5 to 50 mg lipase, about 5 to 50 mg amylase, and about 10 to 100 mg rutin.

3. The method of claim 2, wherein said composition comprises a mixture of about 24 mg trypsin, about 1 mg α-chymotrypsin, about 60 mg papain, about 100 mg pancreatin, about 45 mg bromelin, about 10 mg lipase, about 10 mg amylase, and about 50 mg rutin.

4. A method of treating a patient having acquired immune deficiency syndrome, AIDS, or its precursors, lymphadenopathy syndrome, LAS, or AIDS-related complex, ARC, comprising administering a first composition comprising trypsin, α-chymotrypsin, papain, pancreatin, bromelin, lipase, amylase, and rutin and a second composition comprising trypsin, α-chymotrypsin, papain, and fractionated hydrolysate of calf thymus to the patient.

5. The method of claim 4, wherein said second composition is administered to said patient orally or rectally.

6. The method of claim 5, wherein said first composition comprises a mixture of about 10 to 30 mg trypsin, about 1 to 10 mg α-chymotrypsin, about 40 to 100 mg papain, about 50 to 200 mg pancreatin, about 20 to 100 mg bromelin, about 5 to 50 mg lipase, about 5 to 50 mg amylase, and about 10 to 100 mg rutin, and said second composition comprises a mixture of about 10 to 100 mg trypsin, about 10 to 100 mg α-chymotrypsin, about 50 to 500 mg papain, and about 10 to 100 mg hydrolysate of calf thymus.

7. The method of claim 5, wherein said first composition comprises a mixture of about 24 mg trypsin, about 1 mg α-chymotrypsin, about 60 mg papain, about 100 mg pancreatin, about 45 mg bromelin, about 10 mg lipase, about 10 mg amylase, and about 50 mg rutin, and said second composition comprises a mixture of about 40 mg trypsin, about 40 α-chymotrypsin, about 100 mg papain, and about 40 mg hydrolysate of calf thymus.

8. The method of claim 4, wherein a third composition is administered which comprises trypsin, α-chymotrypsin, papain, and fractionated hydrolysate of calf thymus.

9. The method of claim 8, wherein said third composition is administered to said patient by injection.

10. The method of claim 9, wherein said third composition comprises a mixture of about 1 to 10 mg trypsin, about 1 to 10 mg α-chymotrypsin, about 5 to 50 mg papain, and about 1 to 10 mg hydrolysate of calf thymus.

11. The method of claim 10, wherein said third composition comprises a mixture of about 4 mg trypsin, about 4 mg α-chymotrypsin, about 10 mg papain, and about 3 mg hydrolysate of calf thymus.

12. The method of claim 6, further comprising administering a third composition by injection, wherein said third composition comprises a mixture of about 1 to 10 mg trypsin, about 1 to 10 α-chymotrypsin, about 5 to 50 mg papain, and about 1 to 10 mg hydrolysate of calf thymus.

13. The method of claim 7, further comprising administering a third composition by injection, wherein said third composition comprises a mixture of about 4 mg trypsin, about 4 mg α-chymotrypsin, about 10 mg papain, and about 3 mg hydrolysate of calf thymus.

* * * * *